United States Patent [19]

Veber et al.

[11] Patent Number: 4,656,188
[45] Date of Patent: Apr. 7, 1987

[54] ACE INHIBITORS IN MACULAR DEGENERATION

[75] Inventors: Daniel F. Veber, Ambler; John J. Baldwin, Gwynedd Valley, both of Pa.

[73] Assignee: Merck & Co., Inc., Rahway, N.J.

[21] Appl. No.: 785,925

[22] Filed: Oct. 9, 1985

[51] Int. Cl.[4] .................... A61K 31/195; A61K 31/40; A61K 31/27; A61K 31/505
[52] U.S. Cl. ........................................ 514/423; 514/7; 514/9; 514/213; 514/221; 514/250; 514/259; 514/310; 514/419; 514/490; 514/562; 514/912
[58] Field of Search .................... 514/210, 912, 7, 9, 514/213, 221, 250, 259, 310, 419, 423, 490, 562

[56] References Cited

U.S. PATENT DOCUMENTS 3,995,057 11/1976 Hörrmann ........................ 514/912
4,046,889 9/1977 Ondetti et al. .................... 514/210

OTHER PUBLICATIONS

Igic and Kojovic, *Exp. Eye Res.*, 30, 299–303 (1980).
Chem. Abst. 74:91148w (1971)—Dabis.
Chem. Abst. 96:210615n (1982)—Toshimoto et al.
Chem. Abst. 99:47727b (1983)—Yamagami et al.
Chem. Abst. 101:177530c (1984)—Watkins et al.

*Primary Examiner*—Douglas W. Robinson
*Attorney, Agent, or Firm*—William H. Nicholson; Michael C. Sudol

[57] ABSTRACT

Angiotensin converting enzyme inhibitors are useful in the treatment of senile macular degeneration.

5 Claims, No Drawings

ACE INHIBITORS IN MACULAR DEGENERATION

SUMMARY OF THE INVENTION

This invention is concerned with the use of angiotensin converting enzyme (ACE) inhibitors in the treatment of senile macular degeneration, a leading cause of visual diminution in the elderly.

BACKGROUND OF THE INVENTION

Senile macular degeneration is a poorly characterized disease state of the elderly which appears to result from a poor blood supply to the macular region of the eye. As a result, vision is lost in the central region of the eye while partial peripheral vision is retained. The disease progresses with increased vision loss, one eye at a time. Until the present invention, there was no known treatment of the disease or its symptoms although vasodilators and antihypercholesterolemics have been tried without success.

Experience with ACE inhibitors as antihypertensive agents has shown a tendency for them to accumulate in the eye resulting in unexpectedly high concentrations in ocular tissue [Igic et al., Exp. Eye Res. 30, 299 (1980)]. These high concentrations result in selective ocular vasodilation thereby increasing local blood flow to the otherwise ischemic tissue thus preventing damage to the eye.

It is therefore an object of this invention to provide a novel method of treating senile macular degeneration by the administration of an ACE inhibitor.

It is a further object of this invention to provide pharmaceutical formulations comprising an ACE inhibitor as an active ingredient for use in the novel method of treatment.

DETAILED DESCRIPTION OF THE INVENTION

The novel method of treatment of senile macular degeneration of this invention comprises the administration to a patient in need of such treatment of an effective amount of an angiotensin converting enzyme inhibitor.

The angiotensin converting enzyme inhibitor useful as the active ingredient in the novel method of treatment and pharmaceutical formulations of this invention is selected from: enalapril, enalaprilat, lisinopril, captopril, ranipril, perindopril, zofenopril, quinapril, pentopril, cilazapril, pivopril, fosenopril, indolapril, indalapril, phenacein, fentiapril, alacepril, perinodopril, mugenic acid, ancovenin, CI 925, CGS 14824a, CGS 14831, WY 44221, CI 928, SQ 28853, SQ 27786, CGS 16617, MC 838, K 26,.

The company codes used above serve to identify the compounds designated in the following table:

| Company Code | Chemical Name |
| --- | --- |
| CI-925 | 2-[2-[[1-(1-(ethoxycarbonyl)-3-phenylpropyl]amino]-1-oxopropyl-6,7-dimethoxy-1,2,3,4-tetrahydro-3-isoquinolinecarboxylic acid. |
| CGS-14824a | 3-[[1-ethoxycarbonyl-3-phenyl-(1S)propyl]amino]-2,3,4,5-tetrahydro-2-oxo-1-(3S)—benzazepine-1-acetic acid HCl. |
| CGS-14831 | 3-[[1-carboxylate-3-phenyl-1(S)—propyl]-amino]-2,3,4,5-tetrahydro-2-oxo-1(3S)—benzazepine-1-acetic acid HCl. |
| CI-928 | 2[2-[[1-carbonyl-3-phenylpropyl]-amino]-1-oxopropyl]-1,2,3,4-tetrahydro-3-isoquinoline-carboxylic acid. |
| SQ-28853 | [1-(S)—4S]—4-[[2-[6-(aminosulfonyl)-7-chloro-1,2,3,4-tetrahydro-4-oxo-2-quinazolinyl]ethyl]-thio]-1-(3-mercapto-2-methyl-1-oxo-propyl)-L-proline monosodium salt. |
| SQ-27786 | [1-(s)—4S]—4-[4-[6-(aminosulfonyl)-7-chloro-1,2,3,4-tetrahydro-4-oxo-2-quinazolinylphenoxy]-1-(3-mercapto-2-methyl-1-oxopropyl)-L-proline. |
| MC-838 | Calcium N—[(S)—3-(N—cyclohexane-carbonyl-D-alanylthio)-2-methylpropanoyl]-L-prolinate. |
| K-26 | MeCO—Ile—Tyr—NH—CH(CH$_2$-C$_6$H$_4$-OH)—PO(OH)$_2$ |
| WY-44221 | (−)-(S)—1-[(S)—3-mercapto-2-methyl-1-oxopropyl]indoline-2-carboxylic acid. |
| CGS-16617 | 3-[(5-amino-1-carboxy-1S—pentyl)-amino]-2,3,4,5-tetrahydro-2-oxo-3S—1H—1-benzazepine-1-acetic acid. |

The preferred inhibitors are captopril, disclosed in U.S. Pat. No. 4,046,889, enalapril, enalaprilat or lisinapril disclosed in U.S. Pat. No. 4,374,829, which patents are incorporated herein by reference.

The route of administration can be orally; parenteral injection, for example intravenously, intramuscularly or subcutaneously; or transdermally.

An effective amount of angiotensin converting enzyme inhibitor in the novel method of treatment of this invention is the same as the effective amount normally employed for the treatment of hypertension, i.e. about 0.1 mg to about 1 g and preferably about 5 to 500 mg per day. The dosage regimen can be one to four times a day depending on the daily total required and the unit dosage.

The novel pharmaceutical formulations of this invention for oral administration can be in the form of tablets in combination with other compounding ingredients customarily used, such as, talc, vegetable oils, polyols, benzylalcohols, gums, gelatins, starches or other carriers; dissolved, dispersed or emulsified in a suitable liquid carrier; or in capsules in a suitable encapsulating material. For transdermal administration, the active ingredient can be in the form of an ointment, a gel, a solution, suspension or emulsion in a suitable vehicle or in the form of a patch. For parenteral administration the active ingredient may be dissolved, dispersed, suspended or emulsified with an appropriate injectable vehicle.

EXAMPLE 1

| Dry Filled Capsule | |
| --- | --- |
| | Per Capsule |
| Enalapril | 50 mg |
| Lactose | 149 mg |
| Magnesium Stearate | 1 mg |

| -continued | |
|---|---|
| Dry Filled Capsule | |
| | Per Capsule |
| Capsule (Size No. 1) | 200 mg |

The active compound is reduced to a No. 60 powder and then lactose and magnesium stearate are passed through a No. 60 bolting cloth onto the powder and the combined ingredients are mixed for 10 minutes and filled into the No. 1 dry gelatin capsule.

Any of the other ACE inhibitors can be substituted for enalapril in the above Example 1.

EXAMPLE 2

Tablet

A typical tablet contains captopril (25 mg), pregelatinized starch USP (82 mg), microcrystalline cellulose (82 mg) and magnesium stearate (1 mg). In like manner, for example, N-(1(S)-carboxy-3-phenylpropyl)-L-lysyl-L-proline (20 mg) may be formulated in place of N-(1(S)-ethoxycarbonyl-3-phenylpropyl)-L-alanyl-L-proline with the composition of pregelatinized starch, microcrystalline cellulose and magnesium stearate described above.

Any of the other ACE inhibitors can be substituted for captopril in the above Example 2.

EXAMPLE 3

Injectable

A typical injectable formulation contains enalaprilat (5.42 mg), sodium phosphate diabasic anhydrous (11.4 mg), benzyl alcohol (0.01 ml), and water for injection (1.0 ml). Similarly, this formulation can be prepared employing, for example, N-(1(S)-carboxy-3-phenylpropyl)-L-lysyl-L-proline in place of N-(1(S)-ethoxycarbonyl-3-phenylpropyl)-L-alanyl-L-proline.

What is claimed is:

1. A method of treating senile macular degeneration which comprises the administration to a patient in need of such treatment of 5 to 500 mg per day of an angiotensin converting enzyme inhibitor selected from the group consisting of enalapril, enalaprilat, lisinopril, captopril, ranipril, perindopril, zofenopril, quinapril, pentoapril, cilazapril, pivopril, fosenopril, indoapril, indalapril, phenacein, fentiapril, alacepril, periodopril, mugenic acid, ancovenin, CI 925, CGS 14824a, CGS 14831, WY 44221, CI 928, SQ 28853, SQ 27786, CGS 16617, MC 838, and K 26.

2. The method of claim 1 wherein the angiotensin converting enzyme inhibitor is enalapril.

3. The method of claim 1 wherein the angiotensin converting enzyme inhibitor is lisinopril.

4. The method of claim 1 wherein the angiotensin converting enzyme inhibitor is enalaprilat.

5. The method of claim 1 wherein the angiotensin converting enzyme inhibitor is captopril.

* * * * *